US009194817B2

(12) United States Patent
Sugihara et al.

(10) Patent No.: US 9,194,817 B2
(45) Date of Patent: Nov. 24, 2015

(54) DEFECT DETECTION METHOD

(71) Applicant: NuFlare Technology, Inc., Numazu-shi (JP)

(72) Inventors: Shinji Sugihara, Tokyo (JP); Riki Ogawa, Kanagawa (JP); Hiromu Inoue, Kanagawa (JP)

(73) Assignee: NuFlare Technology, Inc., Numazu-shi (JP)

( * ) Notice: Subject to any disclaimer, the term of this patent is extended or adjusted under 35 U.S.C. 154(b) by 146 days.

(21) Appl. No.: 13/968,816

(22) Filed: Aug. 16, 2013

(65) Prior Publication Data

US 2014/0055774 A1    Feb. 27, 2014

(30) Foreign Application Priority Data

Aug. 23, 2012  (JP) ................................. 2012-184034

(51) Int. Cl.
  *G01N 21/00*   (2006.01)
  *G01N 21/956*  (2006.01)
  *G01N 21/95*   (2006.01)

(52) U.S. Cl.
  CPC ...... *G01N 21/95623* (2013.01); *G01N 21/9501* (2013.01)

(58) Field of Classification Search
  CPC .......... G01N 21/9501; G01N 21/8986; G01N 21/95607; G01N 2021/8825; G01N 21/95623; G01N 21/8851; G01N 21/952; G01N 2021/8854; G01N 2021/8883; G01N 21/8922; G01N 21/9506; G01N 23/225; G01N 27/9046
  See application file for complete search history.

(56) References Cited

U.S. PATENT DOCUMENTS

| 5,537,669 | A  | * | 7/1996 | Evans et al. ................... 382/141 |
| 6,539,106 | B1 | * | 3/2003 | Gallarda et al. .............. 382/149 |
| 7,205,549 | B2 | * | 4/2007 | Yoshida et al. ............... 250/372 |

(Continued)

FOREIGN PATENT DOCUMENTS

| JP | 2002-168799 A | 6/2002 |
| JP | 2008-39712 A  | 2/2008 |
| JP | 4236825       | 12/2008 |

OTHER PUBLICATIONS

Office Action issued Feb. 25, 2015 in South Korean Patent Application No. 2013-0096395 (with English language translation).

(Continued)

*Primary Examiner* — Michael P Stafira
(74) *Attorney, Agent, or Firm* — Oblon, McClelland, Maier & Neustadt, L.L.P.

(57) ABSTRACT

A defect detection method comprising, irradiating light from a light source in an optical system and obtaining a plurality of optical images of a sample having a repeated pattern of a size smaller than a resolution of the optical system; while changing the conditions of the optical system, performing correction processing for the optical images with the use of at least one of a noise filter and a convolution filter; shifting a position of the other optical images based on any of the plurality of optical images, obtaining a relationship between shift amounts of the other optical images and a change of correlation of a gray scale value between the plurality of optical images, and performing positional alignment of the optical images based on the shift amount obtained when the correlation is highest, performing defect detection of the sample with the use of the optical images after the positional alignment.

12 Claims, 5 Drawing Sheets

(56) References Cited

U.S. PATENT DOCUMENTS

| | | | |
|---|---|---|---|
| 8,072,592 B2 * | 12/2011 | Watanabe et al. | 356/237.5 |
| 2006/0002604 A1 * | 1/2006 | Sakai et al. | 382/141 |

OTHER PUBLICATIONS

U.S. Appl. No. 14/020,217, filed Sep. 6, 2013, Ogawa, et al.
U.S. Appl. No. 14/153,199, filed Jan. 13, 2014, Ogawa, et al.
Office Action issued May 21, 2015 in Korean Patent Application No. 2013-0096395 (English-language Translation Only).
Office Action issued Sep. 27, 2014 in Korean Patent Application No. 10-2013-0096395 (with English language translation).
Combined Taiwanese Office Action and Search Report issued Nov. 10, 2014 in Patent Application No. 102128107 (with English language translation).
Timothy F. Crimmins, "Wafer Noise Models for Defect Inspection", Proc. of SPIE vol. 7971, Aug. 2011, 6 pages.

* cited by examiner

DEFECT DETECTION METHOD

CROSS-REFERENCE TO THE RELATED APPLICATION

The entire disclosure of the Japanese Patent Application No. 2012-184034, filed on Aug. 23, 2012 including specification, claims, drawings, and summary, on which the convention priority of the present application is based, are incorporated herein in its entirety.

FIELD OF THE INVENTION

This invention relates to a defect detection method.

BACKGROUND

In a large scale integration circuit (LSI), as the degree of integration and the capacity are increased, the circuit size required for a semiconductor device has been gradually decreasing. For example, the most advanced devices require a line width of a few ten nm.

Enhancement of yield is essential, as the manufacture of LSI requires a large manufacturing cost. In the manufacture of the semiconductor device, a pattern is exposed and transferred onto a resist film formed on a wafer by a reduced projection exposure apparatus generally called a stepper or scanner to form a circuit pattern, using a mask or a reticle (hereinafter collectively referred to as mask) having an original image pattern, whereby the semiconductor device is manufactured. In these circumstances, a pattern defect of the mask constitutes a major cause of reduction in the yield of the semiconductor device.

In these circumstances, the pattern defect of the mask and variation of process terms and conditions at the time of exposure and transfer constitute a major cause of reduction in the yield. Along with miniaturization of an LSI pattern dimension formed on a semiconductor wafer, the size of the pattern defect of the mask is also miniaturized. The dimensional accuracy of the mask is enhanced, whereby the fluctuation of the process terms and conditions is to be absorbed, and thus, in the inspection of the mask, an extremely small pattern defect is required to be detected. The Patent Document 1 (Japanese patent number 4236825) discloses an inspection apparatus for detecting a fine defect on a mask.

Recently, as a technique for forming a fine pattern, nanoimprint lithography (NIL) has attracted attention. In this technique, a template having a nanoscale microstructure is pressured on a specific resist formed on a wafer to form the fine circuit pattern on the resist.

In the nanoimprint technology, to increase productivity, duplicate templates (replica templates) are produced using a master template as an original plate, and the replica templates are used in different nanoimprint apparatuses during forming the fine circuit pattern on the resist. The replica template is required to be produced accurately corresponding to the master template. Thus, high inspection accuracy is required for not only the master template but also the replica template.

A mask is generally formed to have a size four times larger than a circuit size. The size of a pattern of photo-mask is generally four times larger than the size of a circuit pattern formed over the wafer. The pattern is reduced and exposed onto a resist on the wafer by a reduced projection exposure device, using the photo-mask, and thereafter, the circuit pattern is developed. Meanwhile, the patterns of the template in nanoimprint lithography are formed to have the same size as the circuit patterns formed on the wafer. Thus, a shape defect in a pattern of the temperate causes a higher degree of influence to a pattern to be transferred onto the wafer than a shape defect in a pattern of the photo-mask. Accordingly, the detection of a pattern defect of the template is required to be detected with higher accuracy than the detection of the pattern defect of the photo-mask.

However, these days, as the circuit pattern size is being decreased, the pattern size is becoming smaller than the resolution of an optical system of an inspection apparatus used in the detection of a defect. For example, in the case of a line width of a pattern formed on a template being smaller than about 100 nm, the pattern cannot be resolved by a light source using DUV (Deep Ultraviolet radiation) light. Thus, although an EB (Electron Beam) source is used, throughput is low, and a problem arises in that the source cannot be mass-produced.

The present invention has been made in consideration of the above points, and provides a defect detection method in which a defect of a sample having a fine pattern can be detected.

SUMMARY OF THE INVENTION

According to one aspect of the present invention, a defect detection method comprising, irradiating light from a light source in an optical system and obtaining a plurality of optical images of a sample having a repeated pattern having a size smaller than a resolution of the optical system, while changing the conditions of the optical system, performing correction processing for the plurality of optical images with the use of at least one of a noise filter and a convolution filter, shifting a position of the other optical images based on any of the plurality of optical images, obtaining a relationship between shift amounts of the other optical images and a change of correlation of a gray scale value between the plurality of optical images, and performing positional alignment of the plurality of optical images based on the shift amount obtained when the correlation is highest, and performing defect detection of the sample with the use of the plurality of optical images after the positional alignment.

Further to this aspect of the present invention, a defect detection method, wherein the step of performing the defect detection is a step of plotting each pixel of the plurality of optical images in a gray scale value space, and separating a pixel having a defect and a pixel having no defect.

Further to this aspect of the present invention, a defect detection method, wherein the step of separating the pixel having a defect and the pixel having no defect is performed using at least one of: clustering of the each pixel in the gray scale value space, a distance from a correlation straight line of the plurality of optical images to each pixel, and a difference image of the plurality of optical images.

Further to this aspect of the present invention, a defect detection method, wherein the correlation is evaluated using at least one of: a covariance between the plurality of optical images, a correlation coefficient between the plurality of optical images, a sum of square of a difference between the plurality of optical images, and a sum of absolute values of a difference between the plurality of optical images.

Further to this aspect of the present invention, a defect detection method, wherein the plurality of optical images include an optical image imaged by transmission of the irradiated light through the sample and an optical image imaged by reflection of the irradiated light by the sample.

Further to this aspect of the present invention, a defect detection method, wherein the plurality of optical images are captured by changing a focal position between the optical system and the sample.

Further to this aspect of the present invention, a defect detection method, wherein the plurality of optical images include an optical image imaged when the optical system is regarded as a bright field and an optical image imaged when the optical system is regarded as a dark field.

Further to this aspect of the present invention, a defect detection method, wherein the plurality of optical images are captured by changing a polarization state of the light from the light source.

Further to this aspect of the present invention, a defect detection method, further comprising performing correction in which dynamic ranges between the optical images are matched.

Further to this aspect of the present invention, a defect detection method, further comprising performing correction in which a tone of the gray scale value of each of the plurality of optical images is inverted.

Further to this aspect of the present invention, a defect detection method, further comprising correcting an image distortion of the plurality of optical images.

Further to this aspect of the present invention, a defect detection, wherein the light from the light source is DUV (deep ultraviolet radiation) light.

DETAILED DESCRIPTION OF THE EMBODIMENTS

Many of the patterns formed on a wafer are repeated patterns such as line-and-space patterns, that is, a regular pattern repeated with a periodicity. Accordingly, such repeated patterns are formed on a template used in nanoimprint lithography.

When a dense pattern image whose line width is smaller than about 100 nm is to be formed by an optical system using DUV light, even if a lens (numerical aperture NA=1) of theoretical limitation is used, this fine pattern cannot be resolved. However, when such a pattern is the repeated pattern, if line edge roughness increases in a part of the pattern, or if a part of the pattern is lacking, the regularity is disturbed to change a tone of an optical image in the part of the pattern, and therefore, the increase of the line edge roughness and the lack of a part of the pattern can be detected as defects.

However, even if line edge roughness that will not be a defect fluctuates the gray scale value, there is a problem that the fluctuation becomes noise (hereinafter, referred to as base pattern noise); fluctuation is associated with difficulty in discrimination of a defect. As another example of the base pattern noise, there is an example that in a line pattern drawn by electron beam shot, the pattern is distorted by deviation between shots.

While changing the conditions of the optical system, a plurality of optical images having the same pattern are obtained and compared with each other, by doing this a correlation in the base pattern noise can be obtained.

Further, when the conditions of the optical system are suitably set, an image having a low correlation between images regarding a defect can be obtained. By using a difference of the characteristics between such a defect and the base pattern noise, even in a pattern having a size smaller than a resolution limit of the optical system, only the defect can be detected by cancelling the base pattern noise of optical images.

In the above method, positions of the plurality of optical images are required to be precisely aligned. However, unlike the conventional mask inspection, since a pattern is smaller than the resolution limit, there is a problem that the positional alignment cannot be performed based on the pattern. However, as described above, correlation of base pattern noise is obtained under certain conditions.

Accordingly, when the positional alignment of the optical images is performed based on the noise, using the correlation, the positional alignment between images can be performed. Hereinafter, an embodiment of this invention will be described in detail with reference to the drawings.

Figure 1:
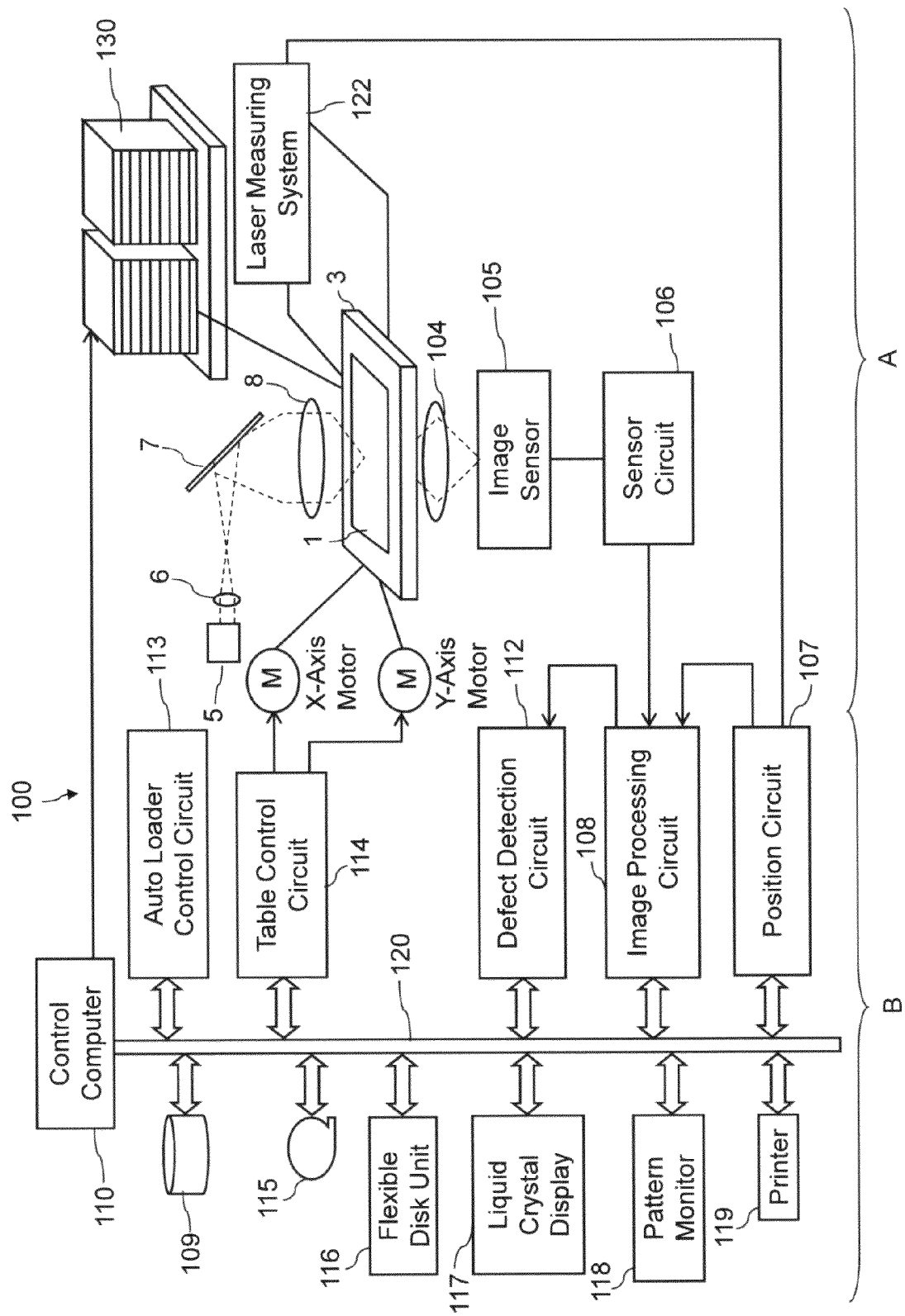
FIG. 1 the inspection apparatus 100 has an optical image acquisition unit A and a control unit B.

FIG. 1 shows an example of an apparatus that is used for the defect inspection method according to the present embodiment. In the present embodiment an optical image of a sample is acquired and any defects are inspected using this apparatus.

As illustrated in FIG. 1, the inspection apparatus 100 has an optical image acquisition unit A and a control unit B.

The optical image acquisition unit A has an optical system consisting of: the light source 5, the lenses 6, 8, and 104, the mirror 7, an image sensor 105, and a sensor circuit 106. Further, the optical image acquisition unit includes an XY stage movable in the horizontal direction (X and Y directions), a laser length measurement unit 122, and an autoloader 130. The XY table 3 has a structure capable of moving in a rotational direction (θ direction).

A sample 1 which is a defect detection target is placed on a Z table (not illustrated) movable in a vertical direction. The Z table is provided on the XY table 3. In the sample 1, a repeated pattern such as a line-and-space pattern, that is, a regular pattern repeated with a periodicity is formed. The sample 1 includes, for example, a template used in the nanoimprint technology.

It is preferable that supporting members provided on the Z table 2 support the sample 1 at three points. When the sample 1 is supported at four points, the height of the supporting member is required to be adjusted with higher accuracy. If the height adjustment is insufficient, the sample 1 may be deformed. On the contrary, according to the three-point support, the sample 1 can be supported while the deformation of the sample is suppressed to a minimum. The supporting member is constituted using a ballpoint having a spherical head surface. Two of the three supporting members are in contact with the sample 1 at the adjacent two corners which are not opposing corners of four corners of the sample 1. The remaining one supporting member is disposed in a region between the two corners where the other two supporting members are not arranged. Each height of the supporting members is adjusted, whereby the sample 1 can be inclined so that the pattern surface P1 coincides with the horizontal surface.

The optical system described above is arranged above and under the sample 1. A resolution limit of the optical system, that is determined by a wavelength (λ) of light from the light source 5 and the numerical aperture (NA) of the lens 104 (R=0.61λ/NA), is larger than a pattern formed in the sample 1.

In this embodiment, a line width of a main pattern formed in the sample 1 can be smaller than approximately 100 nm, and as the light source 5, a light source which irradiates DUV (Deep Ultraviolet radiation) light can be used.

The light emitted from the first light source 5 is transmitted through a lens 6 and the direction of light is changed by a mirror 7, and, thus, is focused on the sample 1 by a lens 8. An image sensor 105 (not illustrated) is disposed under the sample 1, and light transmitted through the sample 1 is imaged on the image sensor 105, so that an optical image (to be described later) is generated.

In this embodiment, light is irradiated from under the sample 1, and reflected light is then focused on the image sensor 105 by a lens.

Figure 2:
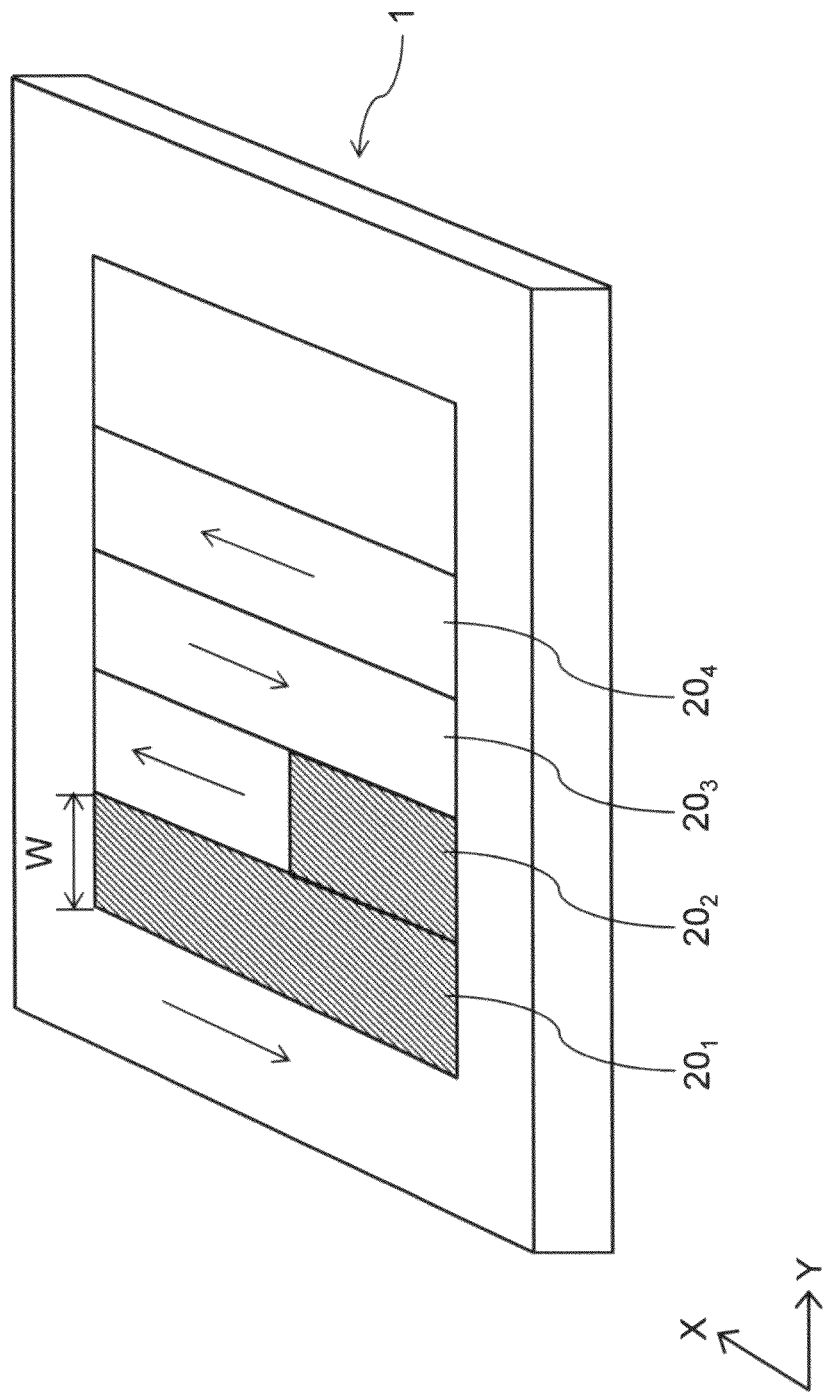
FIG. 2 is a diagram illustrating the way in which an optical image used for inspecting the defects is acquired.

FIG. 2 is a diagram illustrating the way in which an optical image used for inspecting the defects of patterns formed on the sample 1 is acquired.

As illustrated in FIG. 2, the inspection region of the sample 1 is virtually divided into the strip-shaped inspection frames with a scan width W in the Y direction, and the operation of the XY table 3 of FIG. 1 is controlled so that the respective divided inspection frames $20_1$, $20_2$, $20_3$, $20_4$, etc. are continuously scanned, and an optical image is obtained while the XY table 3 moves in the X direction. Then, images with the scan width W illustrated in FIG. 2 are continuously input to the image sensor 105. After an image in the first inspection frame $20_1$ is obtained, images with the scan width W are similarly continuously input while an image in the second inspection frame $20_2$ is moved in the opposite direction this time. When the image in the third inspection frame $20_3$ is obtained, the XY table 3 moves in a direction opposite to the direction in which the image in the second inspection frame $20_2$ is obtained, that is, in the direction in which the image in the first inspection frame $20_1$ has been obtained. The diagonal portion of FIG. 2 schematically represents a region in which an optical image has been obtained as described above.

Next, the control unit B of FIG. 1 will be described.

In the control unit B, a control calculator 110 responsible for the overall control of the apparatus 100 is connected to a position circuit 107, a image processing circuit 108, a defect detection circuit 112, an autoloader control circuit 113, a table control circuit 114, a magnetic disk device 109 as an example of a storage device, a network interface 115, a flexible disk device 116, a liquid crystal display 117, a pattern monitor 118, and a printer 119 via a bus 120 as a data transmission path. The XY table 3 is driven by an X-axis motor and a Y-axis motor controlled by the table control circuit 114. As those motors, a step motor may be used, for example.

As above mentioned, optical acquisition unit A of FIG. 1 acquires an optical image of the sample 1. A specific example of a method of obtaining the optical image will be described as follows.

The sample 1 is placed on the Z table (not shown). The Z table can be moved in a vertical direction by the XY table 3. More specifically, the XY table 3 is driven by the table control circuit 114 under the control of the control calculator 110 and can be moved by a drive unit that drives the XY table 3 in the X and Y directions. The position of the movement of the XY table 3 is measured by the laser length measurement unit 122 and sent to the position circuit 107. The sample 1 on the XY table 3 is automatically conveyed from the autoloader 130 driven by the autoloader control circuit 113, and the sample 1 is automatically discharged after the termination of the inspection.

The light source 5 applies DUV light for defect inspection to the sample 1. The light emitted from the first light source 5 is transmitted through the lens 6 and the direction is changed via the mirror 7, and, thus, is focused on the sample 1 by the lens 8. The distance between the lens 8 and the sample 1 can be adjusted by moving the Z table along the vertical direction.

Light irradiated from the light source 5 and transmitted through the sample 1 is imaged as an optical image on the image sensor 105 through the lens 104.

A procedure of obtaining the optical image in the inspection region of the sample 1 is as described above using FIG. 2. An image of a pattern imaged on the image sensor 105 of FIG. 1 is photoelectrically converted by the image sensor 105 and further A/D (analogue/digital) converted by the sensor circuit 106. As the image sensor 105, a line sensor in which CCD cameras as imaging devices are arranged in a row is used, for example. The line sensor includes a TDI (Time Delay Integration) sensor. A pattern of the sample 1 is imaged by the TDI sensor while the XY table 3 continuously moves in the X-axis direction.

The optical image thus obtained is sent to the image processing circuit 108 of FIG. 1.

In the image processing circuit 108, pixel data in the optical image is represented by the gray scale value of each pixel. For example, any of gradation values 0 to 255 from a gray scale having 256 stages is given to each pixel. In the image processing circuit 108, correction processing (to be described later) applied to the optical image, and the positional alignment between the optical images is performed.

The optical image subjected to the correction processing and the positional alignment in the image processing circuit 108 is sent to a defect detection circuit 112 along with data of the gray scale value. In the defect detection circuit 112, the defect detection of the sample 1 is performed based on data from the image processing circuit 108.

A defect detection method in this embodiment will be described in detail with reference to FIG. 1.

In the defect detection method in this embodiment, at least two optical images are obtained using optical conditions (step 1). The optical conditions include the following.

<Transmission and Reflection>

In the apparatus 100 of FIG. 1, as described above, the light from the light source 5 is irradiated to the sample 1, and the transmitted light is focused on the image sensor 105 through the lens 104, whereby a first optical image is obtained. Meanwhile, light is irradiated from under the sample 1, using an optical system not illustrated in FIG. 1, and the reflected light is focused on the image sensor 105, whereby a second optical image is obtained.

<Focus Conditions>

In FIG. 1, an optical image acquisition unit A has an optical system constituted of the light source 5, the lenses 6, 8, and 104, a mirror 7, the image sensor 105, and a sensor circuit 106. The focus conditions of the sample 1 are changed by a focal position between the sample 1 and the optical system. More specifically, since the sample 1 is placed on the Z table (not illustrated) movable in the vertical direction in FIG. 1, the focal position between the sample 1 and the optical system can be changed by changing the position of the Z table in the vertical direction. For example, the first optical image is obtained in such a state that the Z table is located at a predetermined position, and then the position of the Z table is moved to obtain the second optical image.

<Bright Field and Dark Field>

In FIG. 1, the light from the light source 5 is applied to the sample 1, and the transmission light is focused on the image sensor 105 through the lens 104, whereby the first optical image according to a bright field can be obtained. Light is obliquely applied to the sample 1, using an optical system not illustrated in FIG. 1, and scattered light from the sample 1 are focused on the image sensor 105, whereby the second optical image according to a dark field is obtained.

<Polarization>

The polarization state of light applied to the sample 1 is changed, and the first and second optical images are obtained. The polarization state of light can be changed by providing the optical system, illustrated in FIG. 3, in the optical image acquisition unit A of FIG. 1.

Figure 3:
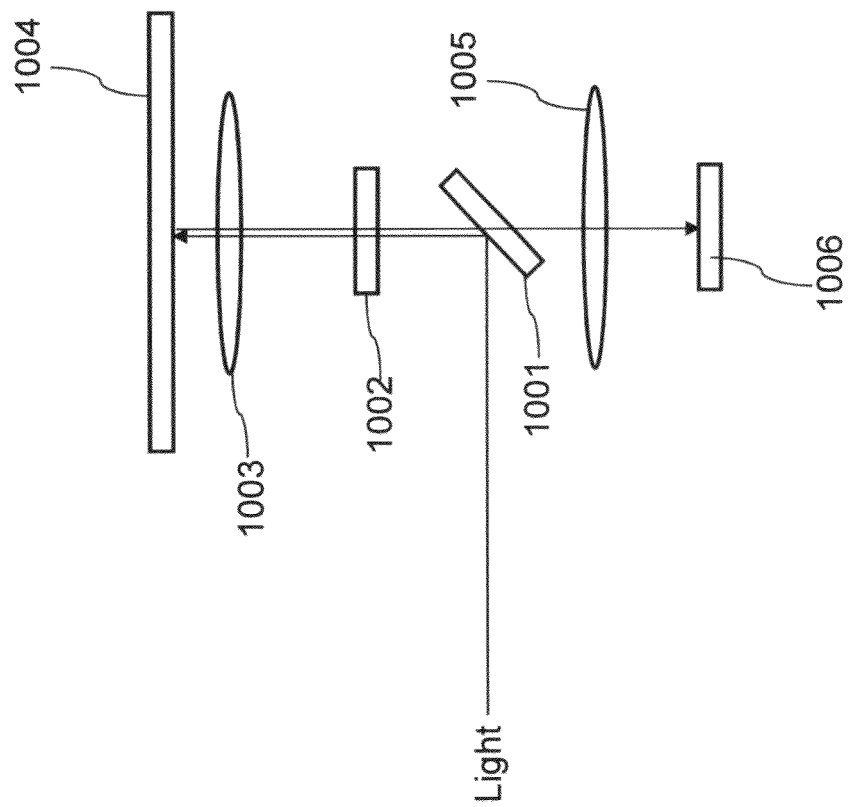
FIG. 3 shows the polarization state of light applied to the sample 1 is changing via the optical system.

In FIG. 3, a light flux of circularly polarized light entering a half mirror 1001 is reflected by a half mirror 1001 and enters a quarter-wave plate 1002. The circularly polarized light is changed to linearly polarized light by the quarter-wave plate 1002 to be converged by a lens 1003, and, thus, to be irradiated to a sample 1004. The light reflected by the sample 1004 transmits through the lens 1003, the quarter-wave plate 1002, and the half mirror 1001 to be converged by a lens 1005, and, thus, to enter a sensor 1006. According to this constitution, the first optical image can be obtained. The angle of the quarter-wave plate 1002 is changed to change incident light and the reference axis of the quarter-wave plate 1002, whereby a polarization direction can be arbitrarily changed. Accordingly, the angle of the quarter-wave plate 1002 is set to an angle different from the angle set when the first optical image is obtained, and the light reflected by the sample 1004 is entered to the sensor 1006 to obtain the second optical image. The sample 1004 can correspond to the sample 1 of FIG. 1, and the sensor 1006 can correspond to the image sensor 105 of FIG. 1.

After the first and second optical images are obtained, the correction processing is applied to the first and second optical images (step 2). More specifically, in the apparatus 100 of FIG. 1, the first and second optical images imaged under different optical conditions are sent from the sensor circuit 106 to the image processing circuit 108.

The reason why the correction is performed in the image processing circuit 108 is as follows.

The first and second optical images obtained in step 1 include not only the base pattern noise but also other noise such as white noise of an image sensor.

Since the first and second optical images are obtained under different conditions, even if the same patterns are imaged, image profiles of the patterns are different from each other. Moreover, positional distortions different from each other may occur. Accordingly, a correction in that the two image profiles become the same, and a correction for the positional distortion are required.

Specific examples of the above correction include the following.

<Noise Filter>

An optical system is considered as a spatial frequency filter and attenuates a signal in a frequency band with not less than a certain frequency. Thus, most of the signals having a high frequency are considered as noise and, more specifically, white noise. Meanwhile, in an optical image, a very gradual variation at a low frequency is sometimes observed. Such high-frequency components and low-frequency components of this image can be attenuated by using a noise filter. The noise filter includes an averaging filter and a band-pass filter, for example.

The averaging filter averages gray scale values of an attention pixel and pixels around the attention pixel, and the obtained value is regarded as the gray scale value of an averaged image.

For example, in an optical image of 512 pixels by 512 pixels, any of gray scale values from 0 to 255 is given to each pixel. The optical image is displayed using gray scale.

When a pixel in i-th row and j-th column of an optical image A is represented by A(i, j), a pixel A' after the averaging processing is represented by the formula (1):

$$A'(i, j) = \sum_{k=-1}^{1} \sum_{l=-1}^{1} A(i+k, J+l)/9 \qquad (1)$$

Meanwhile, a band-pass filter attenuates a low-frequency component and a high-frequency component and passes only a frequency component in a certain band. For example, if the pixel in the i-th row and the j-th column of the optical image A is represented by A(i, j), the pixel A' after the processing using the band-pass filter is represented by the formula (2):

$$A'(i, j) = \sum_{k=-2}^{2} \sum_{l=-2}^{2} \{A(i+k, j+l)f(k+3, l+3)\} \qquad (2)$$

$$f = \begin{pmatrix} -0.01 & -0.01 & -0.01 & -0.01 & -0.01 \\ -0.01 & 0.01 & 0.03 & 0.01 & -0.01 \\ -0.01 & 0.03 & 0.07 & 0.03 & -0.01 \\ -0.01 & 0.01 & 0.03 & 0.01 & -0.01 \\ -0.01 & -0.01 & -0.01 & -0.01 & -0.01 \end{pmatrix}$$

<Convolution Filter>

A convolution filter matches the image profile of the first optical image to the image profile of the second optical image. A difference between the two image profiles is optically interpreted as a difference of PSF (Point Spread Function). Thus, correction processing using a filter imitating PSF, that is, a convolution filter is applied to the two optical images, whereby the optical images can be matched to each other to some extent.

For example, if the pixel in the i-th row and j-th column of the optical image A is represented by A(i, j), the pixel A' after the processing using the convolution filter is represented by the formula (3). A value of PSF can be a predetermined value. Or a value in that a difference between the images after the filter processing is at a minimum, and can then be estimated for each subsequent image. A method for estimating the PSF value in that case includes a least squares method and a maximum likelihood method.

$$A'(i, j) = \sum_{k=-2}^{2} \sum_{l=-2}^{2} \{A(i+k, j+l)PSF(k+3, l+3)\} \qquad (3)$$

$$PSF = \begin{pmatrix} 0.00 & 0.01 & 0.02 & 0.01 & 0.00 \\ 0.01 & 0.06 & 0.10 & 0.06 & 0.01 \\ 0.02 & 0.10 & 0.16 & 0.10 & 0.02 \\ 0.01 & 0.06 & 0.10 & 0.06 & 0.01 \\ 0.00 & 0.01 & 0.02 & 0.01 & 0.00 \end{pmatrix}$$

<Distortion Correction>

Since the second optical image is obtained under optical conditions different from those in the first optical image, different positional distortions may occur in these optical images. Thus, when such a distortion occurs, an amount of distortion in a plane of an optical image, for example, more specifically, an amount of positional movement is linearly corrected.

For example, a distortion amount vector D(i, j) of each pixel (i, j) in an optical image is represented by the formula (4). $(a_1+b_1i+c_1j)$ represents the distortion amount in a horizontal direction (row direction) of an image, and $(a_2+b_2j+c_2i)$ represents the distortion amount in a vertical direction (column direction). $a_1$, $b_1$, $c_1$, $a_2$, $b_2$, and $c_2$ are coefficients representing primary distortion. Those coefficients may be set as fixed values or estimated for each image. Formula (4):

$$D(i,j)=(a_1+b_1i+c_1j, a_2+b_2j+c_2i) \quad (4)$$

A processing of shifting each pixel in each optical image is performed according to the distortion amount vector D obtained as above. The shift by the sub pixel unit (less than 1 pixel) is performed according to a value obtained interpolation processing. As the interpolation processing, bicubic interpolation can be used, for example.

In step 2, in addition to the above correction, it is preferable to perform a correction in which the dynamic ranges between the pixels in the first and second optical images are matched, and to perform tone reversal processing.

<Dynamic Range Correction>

The dynamic ranges of the first and second optical images, that is, correction for matching a ratio of a minimum gray scale value to a maximum gray scale value is performed. More specifically, the first or second optical image is multiplied by a predetermined coefficient. For example, the optical image A is multiplied by a coefficient k, and the optical image A'=kA is obtained. The optical image A' is an optical image after the dynamic range correction. The coefficient k may be a predetermined fixed value. The optimum coefficient k may be obtained for each acquisition of the first and second optical images. The method of obtaining the coefficient k includes, for example, a method of minimizing a difference between a histogram of the gray scale value of the first optical image and a histogram of the gray scale value of the second optical image and a difference of dispersion or a standard deviation of the first and second optical images.

<Tone Reversal>

When there is a negative correlation between the first optical image and the second optical image, the tones of the first and the second optical images are inverted with each other. In order to facilitate positional alignment of the optical images (to be described later) and the comparison between the optical images, it is preferable to invert the tone of any one of the optical images and match the optical image to the other optical image.

For example, if a gray scale values from 0 to 255 is given to each pixel, in order to obtain the optical image A' in which the tone of the optical image A is inverted, it is preferable that the following formula is used.

$$A'=255-A$$

After the correction processing is applied to the first and second optical images as described above, the positional alignment of the optical images is performed in the image processing circuit 108 of FIG. 1 (step 3).

In this embodiment, the positional alignment is performed using the base pattern noise. More specifically, the position of any one of the first and second optical images is slightly shifted with reference to the other optical image. Then, at each position, the correlation of the gray scale values of the first and second optical images, more specifically, the correlation of the base pattern noise is examined. Since the shift amount obtained when the correlation is highest is an optimum positional alignment amount, the positional alignment between the first optical image and the second optical image can be performed using this shift amount. Namely, according to this method, the positional alignment between patterns having a size smaller than a resolution limit of an optical system can be performed.

An index for estimation of the correlation includes the following.

<Covariance>

A covariance is an index indicating two variables (quantitative variables), that is, a magnitude of a covariation between two vectors. In general, when data is given to be $(x_1, y_1)$, $(x_2, y_2)$, ..., and $(x_n, y_n)$, the covariance is represented by the formula (5):

$$S(x, y) = \frac{1}{n}\sum_{i=1}^{n}(x_i - \bar{x})(y_i - \bar{y}) \quad (5)$$

When the two variables have such a relation that the larger one of the variables is, the larger the other variable, as a result the covariance is positive. On the other hand, when the two variables have such a relation that the larger one of the variables is, the smaller the other variable, as a result the covariance is negative. When there is no dependence between the two variables, the covariance approaches 0.

For example, the first optical image A and the second optical image B are represented by vector notation and represented as (V1, V2). At this time, V1 and V2 are represented by the formulae (6) and (7), respectively. The images are square shape, and N represents the size of the image.

$$V1=\{A(1,1), A(1,2), \ldots, A(1,N), A(2,1), \ldots, A(2,N), \ldots, A(N,N)\} \quad (6)$$

$$V2=\{B(1,1), B(1,2), \ldots, B(1,N), B(2,1), \ldots, B(2,N), \ldots, B(N,N)\} \quad (7)$$

The covariance CV between the vector V1 and the vector V2 is represented by the formula (8) where the mean(x) is an average value of x. When an absolute value of the covariance CV is maximum, the correlation between V1 and V2 is the highest. Namely, the shift amount of the second optical image at this time is an optimum value. In this embodiment, the positions of the first and second optical images are aligned with the shift amount.

$$CV=\Sigma\{V1-\text{mean}(V1)\}\{V2-\text{mean}(V2)\}/N^2 \quad (8)$$

The covariance CV is also represented as the formula (9):

$$CV=\text{mean}(V1 \cdot V2)-\text{mean}(V1)\text{mean}(V2) \quad (9)$$

In the formula (9), mean (V1) and mean (V2) are average values of the entire image. Thus, it can be considered that even when an image is shifted, those values are not changed. Accordingly, in the formula (9), a value of the covariance CV in which the correlativity between V1 and V2 is highest can be found by maximizing or minimizing the inner product of V1 and V2 in the first term. The position of the second optical image can be aligned with respect to the position of the first optical image, using the shift amount of the second optical image at this time.

<Correlation Coefficient>

A correlation coefficient is an index representing two variables (quantitative variables), that is, an interrelationship between two vectors. A correlation coefficient CC is given by the formula (10). In the formula (10), std(x) represents a standard deviation of x.

$$CC=CV/\{\text{std}(V1)\text{std}(V2)\} \quad (10)$$

Also in the correlation coefficient, the amount representing a correlation between two optical images is obtained as in the covariance; however, since the results are normalized between −1 to 1, the correlation coefficient has an advantage that the correlation coefficient is more easily handled than the covariance. When the correlation coefficient is used, the shift amount of the second optical image in which the absolute value of the correlation coefficient is at a maximum, is obtained as in the covariance. Then, the positional alignment between the first and second optical images is performed based on the shift amount.

Table 1 shows the examined correlation coefficient of the gray scale value of the first optical image obtained under an optical condition I and the gray scale value of the second optical image obtained under an optical condition II. The optical conditions I and II can be selected from the example described in step 1.

In Table 1, X shift shows the shift amount in the X direction of the second optical image relative to the first optical image in the unit of pixel. Y shift shows the shift amount in the Y direction of the second optical image relative to the first optical image in the unit of pixel.

|  |  | X Shift | | | | | | |
|---|---|---|---|---|---|---|---|---|
|  |  | −3 | −2 | −1 | 0 | 1 | 2 | 3 |
| Y Shift | −3 | 0.19 | 0.20 | 0.13 | 0.08 | 0.12 | 0.20 | 0.21 |
|  | −2 | 0.24 | 0.18 | −0.01 | −0.14 | −0.06 | 0.14 | 0.25 |
|  | −1 | 0.23 | 0.04 | −0.33 | −0.57 | −0.44 | −0.07 | 0.20 |
|  | 0 | 0.20 | −0.08 | −0.59 | −0.91 | −0.75 | −0.26 | 0.14 |
|  | 1 | 0.21 | −0.04 | −0.52 | −0.84 | −0.69 | −0.22 | 0.15 |
|  | 2 | 0.26 | 0.14 | −0.18 | −0.40 | −0.31 | 0.01 | 0.24 |
|  | 3 | 0.26 | 0.26 | 0.13 | 0.02 | 0.07 | 0.21 | 0.28 |

As seen in Table 1, when X shift and Y shift are each 0, the absolute value of the correlation coefficient is at a maximum (0.91). Accordingly, in this case, when the shift amount in the X direction and the shift amount in the Y direction relative to the first optical image are each 0, the positions of these images are ideal.

<Difference Square Sum and Absolute Value Sum>

A sum of square of a difference (SSD) between the first optical image and the second optical image or a sum of absolute value of a difference (SAD) between the first and second optical images is calculated using the formula (11) or (12). In the formula (12), abs(x) represents an absolute value of x.

$$SSD = \Sigma (V1 - V2)^2 \quad (11)$$

$$SAD = \Sigma abs(V1 - V2) \quad (12)$$

Subsequently, the shift amount is obtained when the value of SSD or SAD is at a minimum. The second optical image is aligned with respect to the first optical image by the obtained shift amount of the second optical image.

The correction in step 2 may be performed after step 3. Namely, at least two optical images are obtained using different optical conditions, and then the positional alignment between the first optical image and the second optical image is performed; thereafter, the correction processing may be applied to the first and second optical images.

As described above, after the positional alignment between the first optical image and the second optical image, a defect of the sample 1 is detected using these images (step 4).

In the apparatus 100 of FIG. 1, an optical image subjected to the correction processing and the positional alignment in the image processing circuit 108 is sent to the defect detection circuit 112 along with data of the gray scale value. In the defect detection circuit 112, defect detection for the sample 1 is performed based on the data from the image processing circuit 108. The results of the defect detection are stored in a magnetic disk device 109, as one example.

A specific example of the defect detection method performed in the defect detection circuit 112 includes the following.

<Clustering in Gray Scale Value Space>

As described above, in an optical image, the gray scale value of each pixel of the optical image is varied by fluctuation of the gray scale value caused by line edge roughness or the like. This variation is the base pattern noise. Meanwhile, although the first and second optical images have different optical conditions at the time of imaging, they are obtained by imaging the same pattern; therefore, the base pattern noises of the two optical images are correlated with each other. Thus, if the pixel of each optical image is plotted in the gray scale value space, the positive or negative correlativity should be seen in those optical images.

If the positions of the first and second optical images are not aligned, it is difficult to accurately evaluate the correlativity. On the other hand, if the positions of the two optical images are aligned, the correlativity should be highest. Thus, as described in step 3, the position of the second optical image is shifted with respect to the first optical image, and the positional alignment for these optical images is performed at a position where the correlation between the two optical images is highest. The respective pixels of the first and second optical images at this position are represented in the gray scale value space. More specifically, the gray scale values of the pixels at the same position in those optical images are expressed as the coordinates of the pixels.

Figure 4:
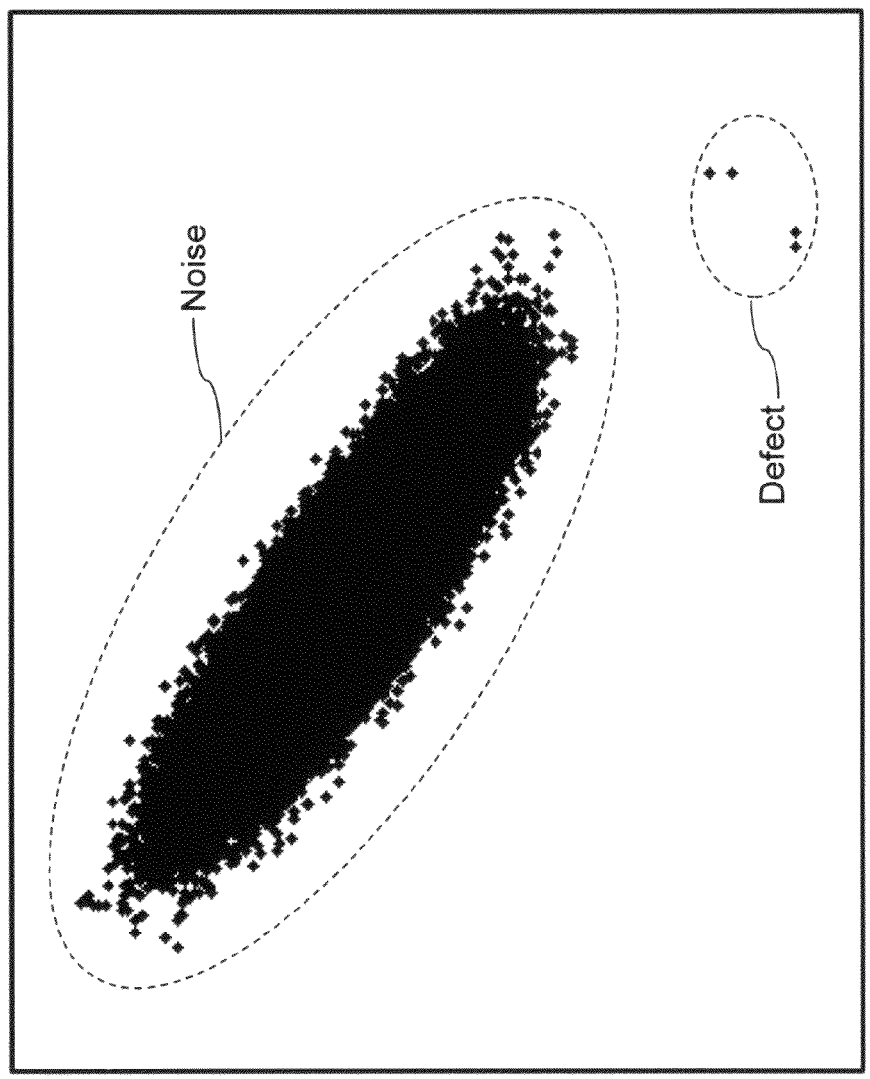
FIG. 4 the pixels having a defect are plotted outside the major data distribution.

For example, when the gray scale value of the first optical image at the coordinates (i, j) is represented as A(i, j) and the gray scale value of the second optical image at the coordinates (i, j) is represented as B(i, j), these gray scale values are represented as (A(i, j), B(i, j)) in the gray scale value space. Thus, similar processing is applied to all pixels, and each obtained point is plotted in the gray scale value space. FIG. 4 shows an example thereof. The horizontal axis of FIG. 4 represents the pixel gray scale value of the first optical image, and the vertical axis represents the pixel gray scale value of the second optical image.

In FIG. 4, a major data distribution is formed by the gray scale value of a pixel having no defect, even though the base pattern noise is seen. In this example, there is a negative correlation between the first optical image and the second optical image. In FIG. 4, data distribution other than the major data distribution can be seen and this corresponds to the gray scale value of a pixel having a defect.

As described above, when the pixels of the two optical images are plotted in the gray scale value space, the pixel having a defect and the pixel having no defect can be separated from each other. Namely, as seen in FIG. 4, the pixels having a defect are plotted outside the major data distribution. Accordingly, the pixels are extracted, whereby a defect can be detected.

The defect detection in this embodiment is not limited to clustering in the gray scale value space, and a method may be employed including a machine-learning algorithm such as a support vector machine (SVM) and a neural network.

The support vector machine includes various methods such as linear support vector machine in which two classes of pattern discriminators are configured using a linear classifier.

As an example of the linear classifier, a binary output value is calculated with respect to an input feature vector, using a discriminant function (linear discriminant function).

$$y = \text{sign}(w^T x + b)$$

W is a parameter vector, and b is a bias parameter. A function sign (u) is a signum function which has 1 when u>0 and has −1 when u≤0. This model outputs 1 when a sum of an inner product of an input vector and a parameter vector and the bias parameter is positive and outputs −1 when the sum is negative. This geometrically corresponds to the fact that an input feature space is divided into two spaces by a discrimination plane.

For example, it is supposed that N feature vectors x1, . . . , and xN and correct class labels t1, . . . , and tN corresponding to the respective feature vectors are given. Further, it is supposed that those feature vectors are linearly separable. Namely, it is assumed that the feature vectors can be separated without error by adjusting the parameter of the linear threshold element well. In general, a parameter for separating the feature vectors without error cannot be uniquely determined. In the support vector machine, such a discrimination plane that a margin from the nearest feature vector is at a maximum is obtained.

When the feature vectors are linearly separable, such a parameter satisfying $$t_i(w^T x_i + b) \geq 1, i=1, \ldots, N$$

exists. This shows that the feature vector is completely separated by two hyperplanes represented by:

$$H_1: w^T x + b = 1$$

$$H_2: w^T x + b = -1$$

and any feature vectors do not exist between the two hyperplanes. In this case, a distance (margin and size) between the discrimination plane and those hyperplanes is:

$$\frac{1}{\|w\|}$$

Accordingly, to obtain the parameters w and b maximizing the margin is equivalent to obtain a parameter minimizing an objective function the following formula is used:

$$L(w) = \tfrac{1}{2} \|w\|^2$$

Under a constraint condition the following formula is used:

$$t_i(w^T x_i + b) \geq 1 (i=1, \ldots, N)$$

The defect can be detected by obtaining a distance from a correlation straight line.

Figure 5:
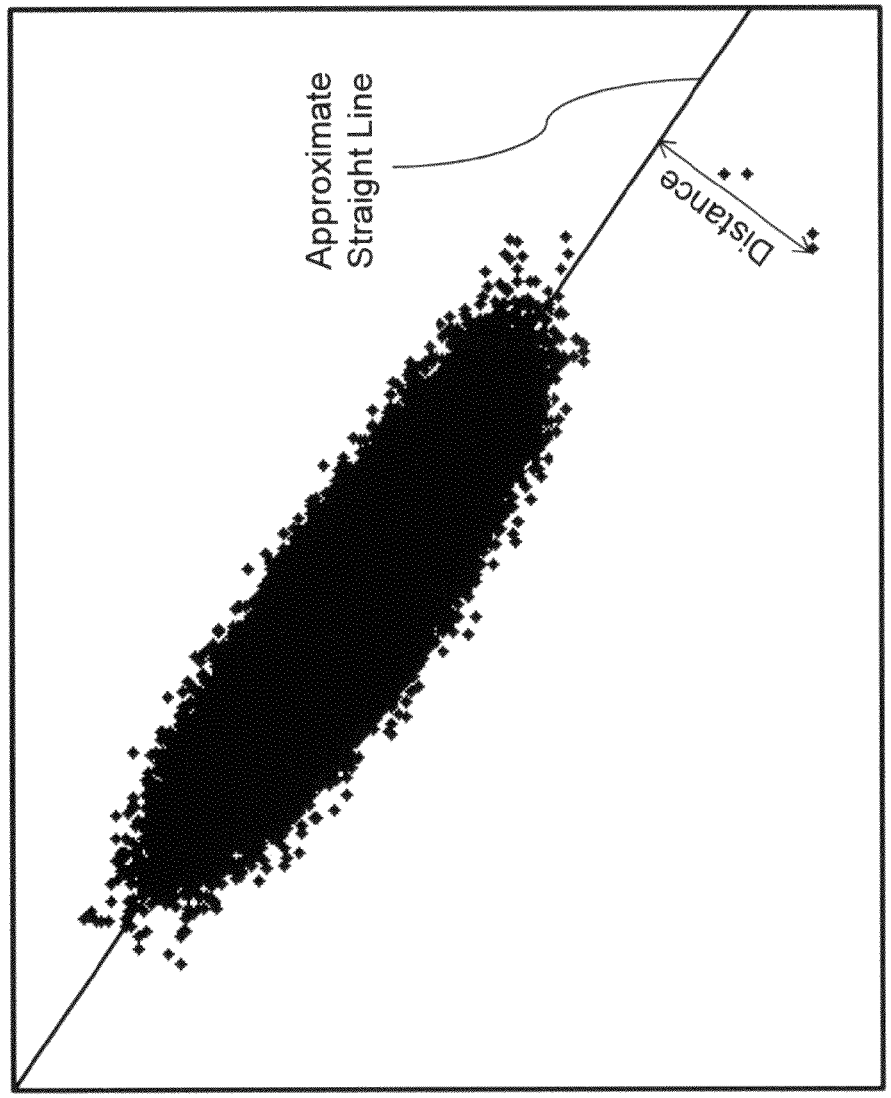
FIG. 5 shows obtaining a distance from the approximate straight line to each point.

For example, in the plot for the gray scale value space as illustrated in FIG. 4, when the first optical image and the second optical image are correlated with each other, an approximate straight line such as a regression line can be drawn. FIG. 5 shows the approximate straight line. As illustrated in FIG. 5, a distance from the approximate straight line to each point (A(i, j), B(i, j)) in a normal direction is obtained, and a pixel whose distance is more than a predetermined value is determined as the pixel having a defect.

A defect can be detected using an image (difference image) corresponding to a difference between the first optical image and the second optical image. More specifically, the defect detection can be performed as follows.

As described in step 1, after the first and second optical images are obtained, the correction processing is applied to these optical images in step 2. Next, as described in step 3, the positional alignment between the first optical image and the second optical image is performed. At this time, correction in which dynamic ranges between the pixels in the first and second optical images are matched and the tone reversal processing are performed. In order to enhance the correlation between the images, convolution correction in step 2 may be performed after the positional alignment. Subsequently, in step 4, the second optical image is subtracted from the first optical image to generate a difference image of them. In the obtained difference image, an average value of the difference image and differences between an each pixel value of the difference image and the average value are obtained. A pixel in which an absolute value of such a difference is more than a predetermined value is determined as the pixel having a defect.

As described above, according to the defect inspection method in this embodiment, even in a pattern having a size smaller than the resolution limit, a defect can be detected. According to this method, in a line-and-space pattern, for example, a defect in which a part of a line is discontinuous can be detected.

Further, in the defect detection method in this embodiment, in an observation optical system for obtaining an optical image of a sample, as light emitted from a light source, DUV (Deep Ultraviolet radiation) light can be used. Accordingly, the defect inspection can be performed without inducing reduction in throughput in comparison with a case where EB (Electron Beam) is used in a light source.

The features and advantages of the present invention may be summarized as follows. This invention can provide a defect detection method that can detect a defect of a minute pattern.

The present invention is not limited to the embodiments described above and can be implemented in various modifications without departing from the spirit of the invention.

For example, in the above embodiment, although the first and second optical images have been described, a plurality of optical images may be provided. For example, a third optical image and a fourth optical image are obtained, whereby the defect detection may be performed using the third and fourth optical images. As the number of optical images increases, the accuracy of the defect detection becomes higher; however, since a time required for processing including correction and positional alignment increases, it is preferable to use a suitable number of optical images while comparing and considering these facts.

The above description of the present embodiment has not specified apparatus constructions, control methods, etc. which are not essential to the description of the invention, since any suitable apparatus constructions, control methods, etc. can be employed to implement the invention. Further, the scope of this invention encompasses all defect inspection methods employing the elements of the invention and variations thereof, which can be designed by those skilled in the art.

What is claimed is:

1. A defect detection method comprising:
   irradiating light from a light source in an optical system and obtaining a plurality of optical images of a sample having a repeated pattern having a size smaller than a resolution of the optical system, while changing the conditions of the optical system;
   performing correction processing for the plurality of optical images with the use of at least one of noise filtering and convolution filtering;
   shifting a position of the other optical images based on any of the plurality of optical images, obtaining a relationship between shift amounts of the other optical images and a change of correlation of a gray scale value using base pattern noise between the plurality of optical images, and
   performing positional alignment of the plurality of optical images based on the shift amount obtained when the correlation is highest; and performing defect detection of the sample with the use of the plurality of optical images after the positional alignment.

2. The defect detection method according to claim 1, wherein the step of performing the defect detection is a step of plotting each pixel of the plurality of optical images in a gray scale value space, and separating a pixel having a defect and a pixel having no defect.

3. The defect detection method according to claim 2, wherein the step of separating the pixel having a defect and the pixel having no defect is performed using at least one of: clustering of the each pixel in the gray scale value space; a distance from a correlation straight line of the plurality of optical images to each pixel; and a difference image of the plurality of optical images.

4. The defect detection method according to claim 1, wherein the correlation is evaluated using at least one of: a covariance between the plurality of optical images; a correlation coefficient between the plurality of optical images; a sum of square of a difference between the plurality of optical images; and a sum of absolute values of a difference between the plurality of optical images.

5. The defect detection method according to claim 1, wherein the plurality of optical images include an optical image imaged by transmission of the irradiated light through the sample and an optical image imaged by reflection of the irradiated light by the sample.

6. The defect detection method according to claim 1, wherein the plurality of optical images are captured by changing a focal position between the optical system and the sample.

7. The defect detection method according to claim 1, wherein the plurality of optical images include an optical image imaged when the optical system is regarded as a bright field and an optical image imaged when the optical system is regarded as a dark field.

8. The defect detection method according to claim 1, wherein the plurality of optical images are captured by changing a polarization state of the light from the light source.

9. The defect detection method according to claim 1, further comprising performing correction in which dynamic ranges between the optical images are matched.

10. The defect detection method according to claim 1, further comprising performing correction in which a tone of the gray scale value of each of the plurality of optical images is inverted.

11. The defect detection method according to claim 1, further comprising correcting an image distortion of the plurality of optical images.

12. The defect detection method according to claim 1, wherein the light from the light source is DUV (deep ultraviolet radiation) light.

* * * * *